(12) United States Patent
Zamir et al.

(10) Patent No.: US 8,546,411 B2
(45) Date of Patent: Oct. 1, 2013

(54) POLYMORPHS OF METHYL (E)-2-{2-[6-(2-CYANOPHENOXY) PYRIMIDIN-4-YLOXY] PHENYL}-3-METHOXYACRYLATE

(75) Inventors: Sharona Zamir, Omer (IL); Inna Faktorovitch, Beer Sheva (IL)

(73) Assignee: Makhteshim Chemical Works Ltd. (IL)

( * ) Notice: Subject to any disclaimer, the term of this patent is extended or adjusted under 35 U.S.C. 154(b) by 151 days.

(21) Appl. No.: 12/525,362

(22) PCT Filed: Aug. 7, 2008

(86) PCT No.: PCT/IL2008/000063
§ 371 (c)(1),
(2), (4) Date: Dec. 7, 2009

(87) PCT Pub. No.: WO2008/093325
PCT Pub. Date: Aug. 7, 2008

(65) Prior Publication Data
US 2010/0173920 A1 Jul. 8, 2010

(30) Foreign Application Priority Data
Feb. 1, 2007 (IL) .......................................... 181125

(51) Int. Cl.
*A01N 43/54* (2006.01)
*A61K 31/505* (2006.01)

(52) U.S. Cl.
USPC .......................................... 514/269; 544/319

(58) Field of Classification Search
USPC ....................................................... 544/319
See application file for complete search history.

(56) References Cited

U.S. PATENT DOCUMENTS

| | | | | |
|---|---|---|---|---|
| 5,145,856 A | * | 9/1992 | Clough et al. | 514/274 |
| 5,160,530 A | * | 11/1992 | Misselbrook et al. | 504/347 |
| 5,760,250 A | * | 6/1998 | Jones et al. | 549/305 |
| 6,153,750 A | * | 11/2000 | Whitton et al. | 544/312 |
| 6,162,916 A | * | 12/2000 | Whitton et al. | 544/319 |
| 6,162,945 A | | 12/2000 | Keil et al. | |
| 6,163,945 A | | 12/2000 | Amano et al. | |
| 7,084,272 B2 | | 8/2006 | Jackson et al. | |
| 2002/0042514 A1 | * | 4/2002 | Doyle et al. | 544/334 |
| 2004/0092746 A1 | * | 5/2004 | Clough et al. | 546/256 |
| 2004/0242607 A1 | * | 12/2004 | Jackson et al. | 514/269 |
| 2006/0229450 A1 | * | 10/2006 | Jackson et al. | 544/314 |
| 2008/0214587 A1 | * | 9/2008 | Whitton et al. | 514/269 |
| 2010/0036124 A1 | * | 2/2010 | Beveridge et al. | 544/319 |

FOREIGN PATENT DOCUMENTS

| | | |
|---|---|---|
| EP | 0242081 | 10/1987 |
| EP | 0382375 | 8/1990 |
| IN | 179039 | 2/1994 |
| WO | WO 9208703 A1 * | 5/1992 |
| WO | 9701538 | 1/1997 |
| WO | 98/07707 A1 | 2/1998 |
| WO | 9818767 | 5/1998 |
| WO | 02100837 | 12/2002 |
| WO | 2006114572 A2 | 11/2006 |
| WO | 2008043977 A1 | 4/2008 |
| WO | WO2008/075341 A1 | 6/2008 |

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
H.G. Brittain, Preparation and Identification of Polymorphs and Solvatomorphs in, Preformulation in Solid Dosage Form Development, 185-228 (5th ed., M. C. Adeyeye et al., eds., 2008).*
Haleblian, John, and McCrone, Walter, "Pharmaceutical Applications of Polymorphism", Journal of Pharmaceutical Sciences, 1969, 58(8), 911-929.*
Gu, Chong-Hui, et al., "Polymorph Screening: Influence of Solvents on the Rate of Solvent-Mediated Polymorphic Transformation", Journal of Pharmaceutical Sciences, 2001, 90(11) 1878-1890.*
Stahly, G. Patrick, "Diversity in Single- and Multiple-Component Crystals. The Search for and Prevalence of Polymorphs and Cocrystals", Crystal Growth & Design, 2000, 7(6), 1007-1026.*
Rustichelli, C., et al., "Solid-state study of polymorphic drugs: carbamazenpine", Journal of Pharmaceutical and Biomedial Analysis, 2000, 23, 41-54.*
Schott, Hans, "Colloidal Dispersions", Remington: Practice of the Science and Pharmacy, 19th Ed. Chapter 20, Mack Publishing, Easton PA, 1995, 252-277.*
Radebaugh Galen W. and Ravin, Louis J., "Preformulation", Remington: Practice of the Science and Pharmacy, 19th Ed. Chapter 83, Mack Publishing, Easton PA, 1995, 1447-1462.*
O'Connor, Robert E., et al., "Powders", Remington: Practice of the Science and Pharmacy, 19th Ed. Chapter 91, Mack Publishing, Easton PA, 1995, 1598-1614.*
WO9730020, published Aug. 21, 1997, Abstract Only, 1 page.
Brighton Crop Protection Conference (Pests and Diseases) 1992, vol. 1, 5 6, pp. 435 442.

(Continued)

*Primary Examiner* — James O Wilson
*Assistant Examiner* — Alexander R Pagano
(74) *Attorney, Agent, or Firm* — Cantor Colburn LLP

(57) ABSTRACT

The present invention relates to novel crystalline polymorphic and amorphous forms of the compound methyl (E)-2-{2-[6-(2-cyanophenoxy)pyrimidin-4-yloxy]phenyl}-3-methoxy-acrylate (azoxystrobin). Infrared Raman spectra, X-ray powder diffraction pattern and differential scanning calorimetry thermogram of two polymorphs "A" and "B" are provided. Further, the present invention also provides methods for preparing the novel polymorphic forms "A" and "B", as well as processes for producing mixtures of the polymorphs, and a process for preparing amorphous azoxystrobin. Yet further, the present invention provides anti-fungal compositions comprising the novel crystalline polymorphs "A" and "B" or amorphous azoxystrobin, which are useful for controlling and combating fungi grown on agricultural and horticultural crops and up-land, and methods of using the same as pesticidal agents for combating fungi on agricultural and horticultural crops.

17 Claims, 10 Drawing Sheets

(56) References Cited

OTHER PUBLICATIONS

The Pesticide Manual, published by the British Crop Protection Council, (2000) 12th edition, pp. 54 55.
Clough, J.M., et al., "Azoxystrobin: A Novel Broad-Spectrum Systemic Fungicide", Pesticide Outlook, Aug. 1996, p. 16-20.
Communiction pursuant to Rule 114(2) EPO. Observations by third party concerning EP 08702644.9, dated Nov. 9, 2009.
Braga, Dario and Grepioni, Fabrizia, "Making crystals from crystals: a green route to crystal engineering and polymorphism", Chem. Commun. p. 3635-3645, (2005).
Braga, Dario , et al., "Crystal Polymorphism and multiple crystal forms", Struct Bond, vol. 132, p. 25-50 (2009).
Braga, Dario and Grepioni, Fabrizia, Chapter 8: "Polymorphism, Crystal Transformations and Gas-Solid Reactions", Crystal Design: Structure and Function, vol. 7, p. 325-373 (2003).
Caira, Mino R., "Crystalline polymorphism of Organic Compounds", Topics in Current Chemistry, vol. 198, p. 163-208 (1998).
Laird, Trevor, "Polymorphism—Still Unpredictable", Organic Process Research & Development 2010, vol. 14, No. 1, p. 1 (Editorial), (2010).
Nangia, Ashwini and Desiraju, Gautam R., "Pseudopolymorphism: occurrences of hydrogen bonding organic solvents in molecular crystals", Chem. Commun., p. 605-606 (1999).
van Tonder, Elsa C., et al. "Preparation and Physicochemical Characterization of 5 Niclosamide Solvates and 1 Hemisolvate", AAPS PharmSciTech, vol. 5, No. 1, p. 1-10 (2004).
Desikan, Sridhar, et al., "Process Developement Challenges to Accommodate a Late-Appearing Stable Polymorph: A Case Study on the Polymorphism and Crystallization of a Fast-Track Drug Development Compound", Organic Process Research & Development, 2005, 9, 933-942.
Roy, Saikat and Matzger, Adam J., "Unmasking a Third Polymorph of a Benchmark Crystal-Structure-Prediction Coumpound", Angewandte Chemie Int. Ed., 2009, 48, 8505-8508.
Cabri, Walter, et al., "Polymorphisms and Patent, Market, and Legal Battles: Cefdinir Case Study", Organix Process Research & Development, 2007, 11, 64-72.
International Preliminary Report on Patentability and Written Opinion of the International Searching Authority for PCT/IL2008/000063, Aug. 4, 2009, 6 pages.
International Search Report for PCT/IL2008/000063, mailed Apr. 17, 2009, 2 pages.
Jain, N.K. and Mohammedi, M.N., "Polymorphism in Pharmacy" Indian Drugs 1986, 23(6), 315-329.
Liebenberg, Wilna, "Crystal Polymorphism and its Occurance Among Active Pharmaceutical Ingredients in South Africa", North-West University, South Africa, May 6, 2005, 1-27.
Newman, Ann W. and Byrn, Stephen R., "Solid-state analysis of the active phamaceutical ingreident in drug products", Drug Discovery Today, vol. 8, No. 19, Oct. 2003, 898-905.
Papathoma, Sofia, "Patenting Polymorphs at the European Patent Office", presentation Barcelona, Spain, Jun. 19-21, 2006, 1-14.
T077/88 Board of Appeals of the European Patent Office, Decision of May 24, 2011, for Application No. 01116338.3, 1-27.
Translation of Notice of Rejection (1st Office Action) for Japanese Patent Application No. 2009-547809, mailed Dec. 18, 2012, 3 pages.
Third party observation to European Patent Application No. 08702644.9, mailed Oct. 29, 2012, 7 pages.
Brittain, Harry G. and Fiese, Eugene F., "Effects of Pharmaceutical Processing on Drug Polymorphs and Solvates" in H.G. Brittian (ed.) Polymorphism in Pharmaceutical Solids, Chapter 8, Marcel Dekker, Inc., New York, 1999, 331-361.

\* cited by examiner

US 8,546,411 B2

POLYMORPHS OF METHYL (E)-2-{2-[6-(2-CYANOPHENOXY)PYRIMIDIN-4-YLOXY]PHENYL}-3-METHOXYACRYLATE

FIELD OF THE INVENTION

The present invention relates to novel crystalline polymorphs and an amorphous form of methyl (E)-2-{2-[6-(2-cyanophenoxy)pyrimidin-4-yloxy]phenyl}-3-methoxyacrylate (azoxystrobin), to processes for their preparation, compositions comprising the new forms, and their use as fungicidal agents.

BACKGROUND OF THE INVENTION

The strobilurin fungicide methyl (E)-2-{2-[6-(2-cyanophenoxy)pyrimidin-4-yloxy]phenyl}-3-methoxyacrylate (azoxystrobin), known by the common name azoxystrobin, is a widely used commercial agrochemical product. It is described in "The Pesticide Manual" published by the British Crop Protection Council, 12$^{th}$ edition, pp 54-55 and in the proceedings of the Brighton Crop Protection Conference (Pests and Diseases) 1992, Volume 1, 5-6, pp 435-442. It was first disclosed in EP-A-0382375 (compound 9, Example 3) along with methods for its preparation.

Azoxystrobin was first marketed in 1998 and is a systemic, broad-spectrum fungicide with activity against the four major groups of plant pathogenic fungi including Ascomcetes (e.g., powdery mildews), Basidiomycetes (eg rusts), Deutoromycetes (e.g., rice blast) and Oomycetes (e.g., downy mildew). It inhibits spore germination and mycelial growth. It has worldwide uses on cereals, vines, rice, citrus, potatoes and tomatoes. In 1999, azoxystrobin was the leading proprietary fungicide worldwide and is now a world market leader in cereals.

There are several reported ways of making azoxystrobin. Several methods are based on the construction of the methyl α-phenyl-β-methoxyacrylate group at an early stage followed by building the central pyrimidinyloxy and terminal cyanophenoxy rings. For example, (E)-methyl 2-(2-hydroxyphenyl)-3-methoxyacrylate may be reacted with 4,6-dichloropyrimidine under alkaline conditions in N,N-dimethylformamide to form (E)-methyl 2-[2-(6-chloropyrimidin-4-yloxy)phenyl)-3-methoxyacrylate which is then reacted with 2-cyanophenol in an Ullmann-type coupling process (see EP-A-0382375). The (E)-methyl 2-(2-hydroxyphenyl)-3-methoxyacrylate may be prepared by the formylation and subsequent methylation of methyl 2-benzyloxyphenylacetate followed by removal of the benzyl protecting group (see EP-A-0242081). Formylation and methylation techniques for preparing the methyl α-phenyl-β-methoxyacrylate group are also described in WO 97/30020 and WO 97/01538.

U.S. Pat. No. 7,084,272 discloses an alternate method for preparing azoxystrobin by constructing the methyl-α-phenyl-β-methoxyacrylate group after building on the central pyrimidinyloxy ring or the central pyrimidinyloxy ring and terminal cyanophenol ring. Reportedly, this avoids a Smiles-type rearrangement and delivers the desired E-isomer.

There is an urgent and unmet need in the art for efficient methods for the preparation and purification of azoxystrobin, which are simple and can be used on a large scale for industrial manufacture, and which produce highly pure product that can be safely utilized.

SUMMARY OF THE INVENTION

The present invention relates to novel crystalline polymorphic and amorphous forms of methyl (E)-2-{2-[6-(2-cyanophenoxy)pyrimidin-4-yloxy]phenyl}-3-methoxyacrylate (azoxystrobin). The present invention also provides methods for preparing the forms, as well as pharmaceutical compositions comprising same, and methods of using same as pesticidal agents for combating fungi on agricultural and horticultural crops.

In one embodiment, the present invention provides a novel crystalline polymorphic form of azoxystrobin, designated "Form A". Form A exhibits an X-ray powder diffraction pattern substantially as shown in FIG. 1, having characteristic peaks (expressed in degrees 2θ (+/−0.2°θ) at one or more of the following positions: 6.25, 13.8, 17.65, 19.05, 26.4, and 28.5. Form A typically exhibits additional minor peaks at 11 and 14.4 degrees 2θ (+/−0.2°θ). Form A also exhibits an infrared (IR) spectrum substantially as shown in FIG. 2, having characteristic peaks at about 1378, 1328 and 1154 cm$^{-1}$. Form A also exhibits a Differential Scanning Calorimetry (DSC) thermogram substantially as shown in FIG. 3, which is characterized by a predominant endotherm peak in the range of about 114-117° C. as measured by Differential Scanning Calorimeter at a scan rate of 10° C. per minute. Form A also exhibits a Raman spectrum substantially as shown in FIG. 4, having characteristic peaks at about 4398, 1329 and 2232 cm$^{-1}$.

In another embodiment, the present invention provides a novel crystalline polymorphic form of azoxystrobin designated "Form B". Form B exhibits an X-ray powder diffraction pattern substantially as shown in FIG. 5, having characteristic peaks (expressed in degrees 2θ (+/−0.2°θ) at one or more of the following positions: 7.5, 11.75, 13.20 and 19.65. Form B typically exhibits additional minor peaks at 14.15, 17.1 and 23.6 degrees 2θ (+/−0.2°θ). Form B also exhibits an IR spectrum substantially as shown in FIG. 6, having characteristic peaks at about 1389, 1335 and 1245 cm$^{-1}$. Form B also exhibits a DSC thermogram substantially as shown in FIG. 7, which is characterized by a predominant endotherm in the range of about 101-105° C., as measured by Differential Scanning Calorimeter at a scan rate of 10° C. per minute. Form B also exhibits a Raman spectrum substantially as shown in FIG. 8, having characteristic peaks at about 3098, 1335 and 2237 cm$^{-1}$.

In yet another embodiment, the present invention provides a mixture of polymorphic Form A and Form B of azoxystrobin. The mixture exhibits a DSC thermogram substantially as shown in FIG. 9, as measured by Differential Scanning Calorimeter at a scan rate of 10° C. per minute.

In another embodiment, the present invention provides a novel amorphous azoxystrobin, which exhibits an X-ray powder diffraction pattern substantially as shown in FIG. 10.

In another aspect, the present invention provides processes for preparing the novel polymorphs of azoxystrobin Form A and Form B, as well as processes for producing mixtures of the polymorphs, and a process for preparing amorphous azoxystrobin.

In one embodiment, Form A azoxystrobin can be prepared by crystallizing azoxystrobin from a solvent selected from the group consisting an alcohol, an ether, a ketone, an ester, an amide, a nitrile, and an aliphatic or aromatic hydrocarbon; and isolating the resulting crystals. In a currently preferred embodiment, the solvent is selected from the group consisting of methanol, ethanol, tetrahydrofuran, acetone, ethylene glycol, acetonitrile, ethyl acetate, methyl isobutyl ketone, xylene and toluene. In another currently preferred embodiment, the process includes preparing a solution of azoxystrobin in one or more of the aforementioned solvents, preferably by applying heat until dissolution is complete, gradually cooling the solution until crystals appear (e.g., by removing the heat and allowing the solution to gradually cool), and isolating the crystals.

In one embodiment, Form B azoxystrobin can be prepared by crystallizing azoxystrobin from a solvent mixture comprising water and an organic solvent selected from the group consisting of an alcohol and an amide; and isolating the resulting crystals. In a currently preferred embodiment, the organic solvent is selected from the group consisting of 1-propanol and N,N-dimethyl acetamide. In another currently preferred embodiment, the process includes preparing a solution of the compound in one or more of the aforementioned organic solvents, with or without applying heat until dissolution is complete, adding water (preferably pre-cooled) so as to form crystals of the compound, and isolating the crystals.

In another embodiment, a mixture of Form A and Form B azoxystrobin can be prepared by crystallizing azoxystrobin from a solvent mixture comprising an alcohol (e.g., isopropyl alcohol, 1-propanol and butanol) and an anti-solvent selected from an aliphatic and aromatic hydrocarbon (e.g., heptane); and isolating the resulting crystals.

In a currently preferred embodiment, the process includes preparing a solution of azoxystrobin in an alcohol, preferably by applying heat until dissolution is complete, adding the anti-solvent so as to form crystals of the compound, and isolating the crystals. In another embodiment, a mixture of Form A and Form B azoxystrobin can be prepared by a) preparing a solution of methyl (E)-2-{2-[6-(2-cyanophenoxy)pyrimidin-4-yloxy]phenyl}-3-methoxyacrylate in an alcohol (e.g., isopropyl alcohol); b) rapidly cooling the solution so as to form crystals of said compound (e.g., by placing the solution in a cold water or ice bath); and isolating the crystals.

In one embodiment, amorphous azoxystrobin is prepared by heating azoxystrobin to a temperature greater than its melting point (preferably to a temperature of about 120° C. or greater), and cooling as fast as possible (e.g., quenching to ice-acetone bath).

In another aspect, the present invention provides anti-fungal compositions comprising the novel crystalline polymorphs or amorphous azoxystrobin, which are useful for controlling and combating fungi grown on agricultural and horticultural crops and up-land. In one embodiment, the compositions comprise a crystalline polymorph Form A azoxystrobin; and an acceptable adjuvant. In another embodiment, the composition comprises a crystalline polymorph Form B of azoxvstrobin: and an acceptable adjuvant. In another embodiment, the composition comprises a mixture of a crystalline polymorph Form A and B of azoxystrobin; and an acceptable adjuvant. In one embodiment, the compositions comprise an amorphous azoxystrobin; and an acceptable adjuvant.

The present invention also relates to methods for combating fungus in a plant, comprising applying to the plant, to the seed of the plant or to the locus of a seed or plant a fungicidally effective amount of the compositions of the invention.

The present invention also relates to methods for protecting crops and upland, including industrial products thereof, such as seeds and fruits, by applying to the crops or products thereof an effective amount of the compositions of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
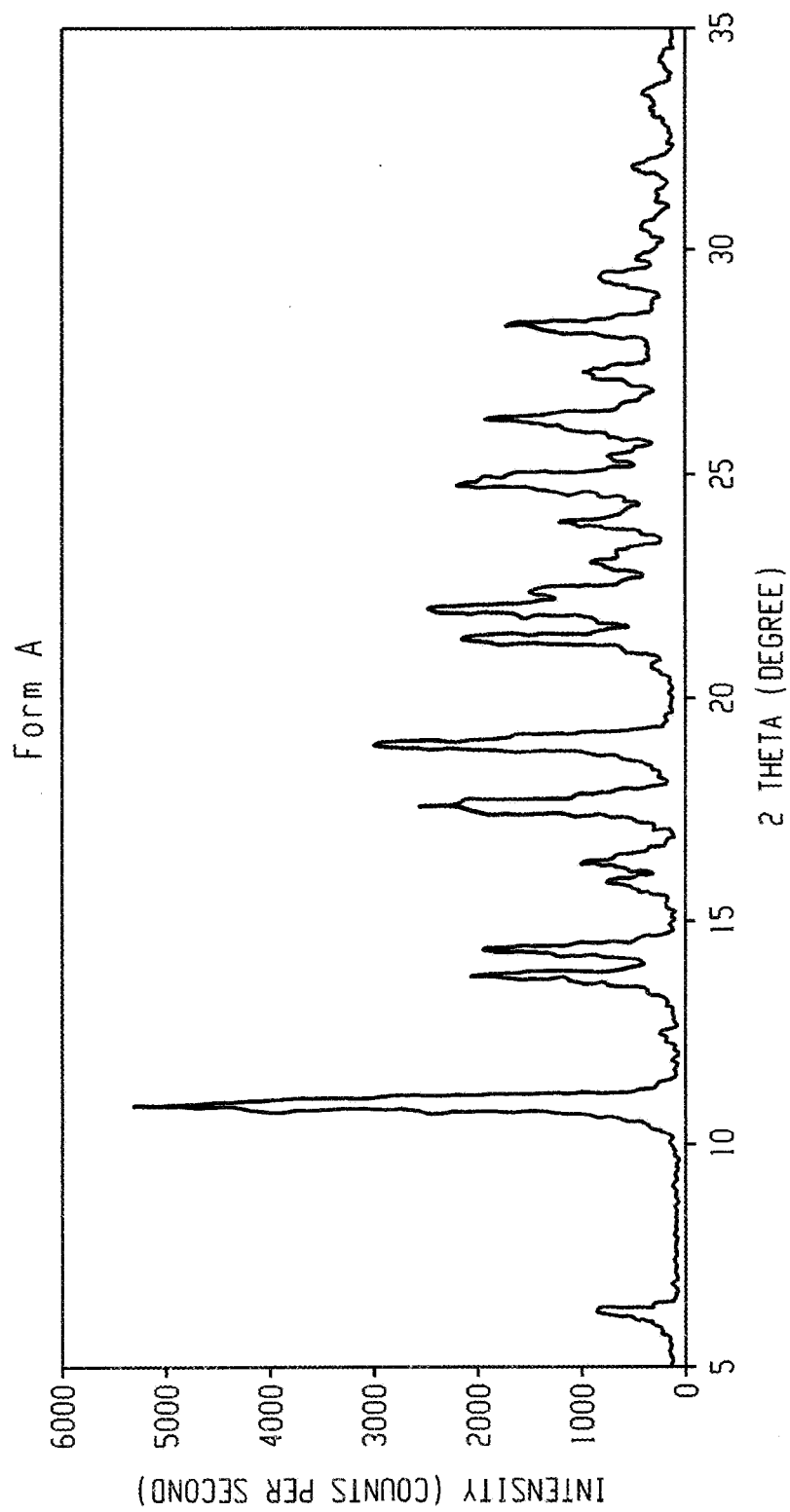
FIG. 1 is an X-ray powder diffraction spectrum of azoxystrobin Form A.

The present invention is generally directed to novel crystalline polymorphic forms of methyl (E)-2-{2-[6-(2-cyanophenoxy)pyrimidin-4-yloxy]phenyl}-3-methoxyacrylate (azoxystrobin) referred to herein as "polymorph Form A" and "polymorph Form B", and to mixtures of said polymorphs. The present invention also relates to an amorphous form of azoxystrobin. The present invention also provides methods for preparing the novel polymorphs and amorphous form, as well as to pharmaceutical compositions comprising same, and methods of use thereof for combating noxious livings on agricultural and horticultural crops.

Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. Furthermore, the metastable form, although less stable, may exhibit properties desirable over those of the stable form, such as better formulative ability, improved dispersability in water and the like.

To the applicant's best knowledge, in the case of methyl (E)-2-{2-[6-(2-cyanophenoxy)pyrimidin-4-yloxy]phenyl}-3-methoxyacrylate(azoxystrobin), no crystalline forms are known.

The inventors of the present applications, after extensive experimentation, have discovered two new crystalline forms of azoxystrobin, designated Form A and Form B. The inventors have further discovered a novel amorphous form of azoxystrobin. These new forms exhibit different spectral characteristics as depicted by their distinct Differential Scanning Calorimetry (DSC) thermograms, X-ray diffraction patterns, infrared (IR) spectra and Raman spectra.

Form A

In one embodiment, the present invention provides a novel crystalline polymorphic form of methyl (E)-2-{2-[6-(2-cyanophenoxy)pyrimidin-4-yloxy]phenyl}-3-methoxyacrylate (azoxystrobin), designated "Form A". This novel and surprising polymorph may be characterized by, for example, by DSC, X-Ray powder diffraction spectrometry, IR spectrometry and/or Raman spectrometry.

For example, as shown in FIG. 1, Form A exhibits an X-ray powder diffraction pattern having characteristic peaks (expressed in degrees 2θ+/−0.2°θ) at one or more of the following positions: 6.25, 13.8, 17.65, 19.05, 26.4, and 28.5. Form A typically exhibits additional minor peaks at 11 and 14.4 degrees 2θ (+/−0.2°θ). The X-Ray powder diffraction were collected on Philips powder diffractometer PW 1050/70 operated at 40 kV and 30 mA using CuKα radiation (wavelength equal to 1.54178 Å) and diffracted beam graphite monochromator. The typical θ-2θ scan range is 3-35° 2 Theta with a step size of 0.05° and a count time of 0.5 seconds per step.

The samples were grinded using agate mortar and pestle. The obtained powder is then pressed into aluminum sample holder with rectangular cavity of 20 mm*15 mm and of 0.5 mm depth.

Figure 2:
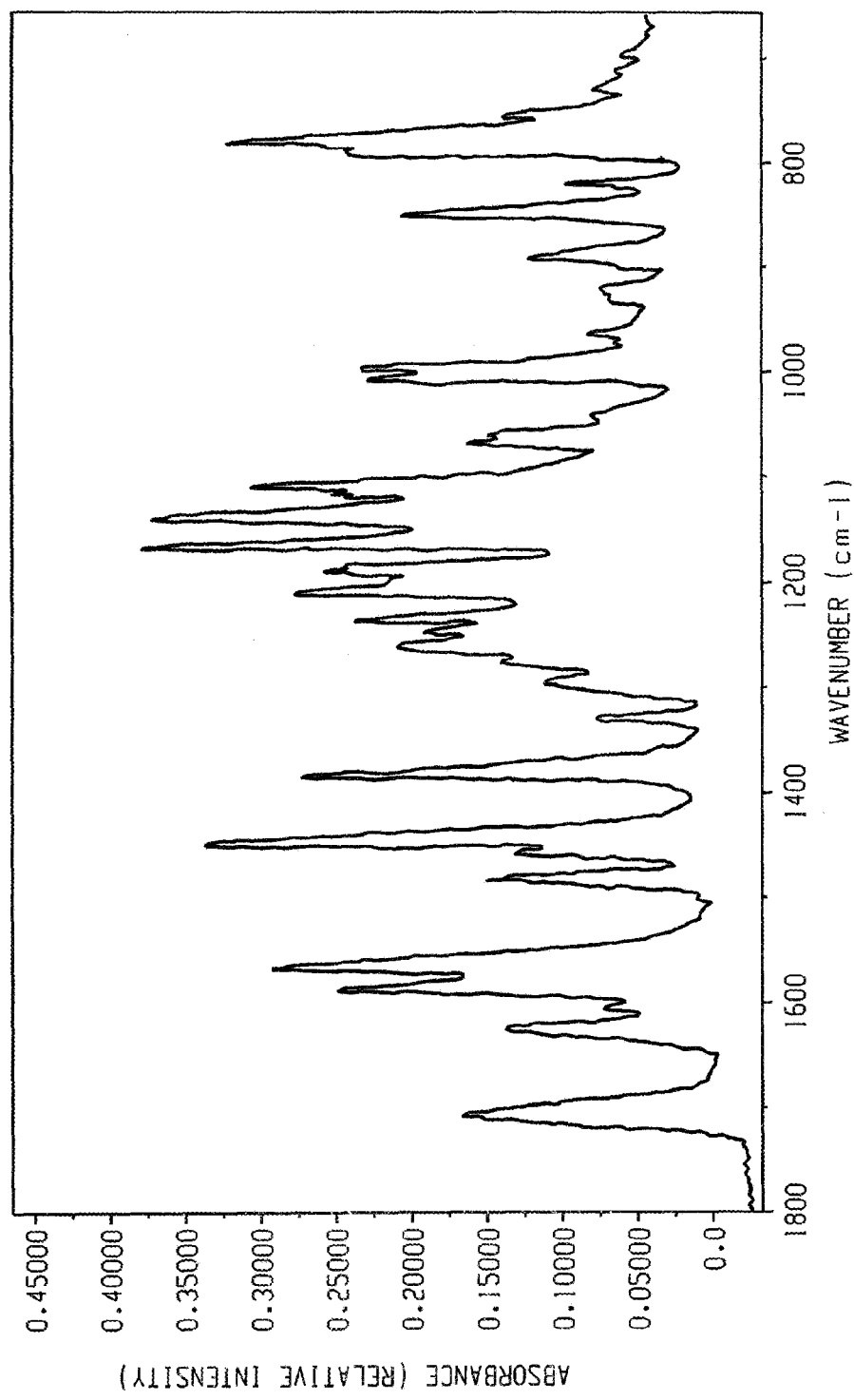
FIG. 2: is a FT Infrared spectrum of azoxystrobin Form A.

Furthermore, as shown in FIG. 2, Form A also exhibits an Infrared (IR) spectrum having characteristic peaks at about 1378, 1328 and 1154 cm$^{-1}$, as measured by a Fourier transform infrared (FT-IR) spectrophotometer ReactIR™ 1000 of Mettler Toledo Autochem (ATR method, MCT detector), diamond window, in DuraSamplIR™ sampling device. The diamond sensor has a standard focusing optic of ZnSe. The powdered samples were compressed in the sampling device and were measured with resolution of 4 cm$^{-1}$ and 256 scans.

Figure 3:
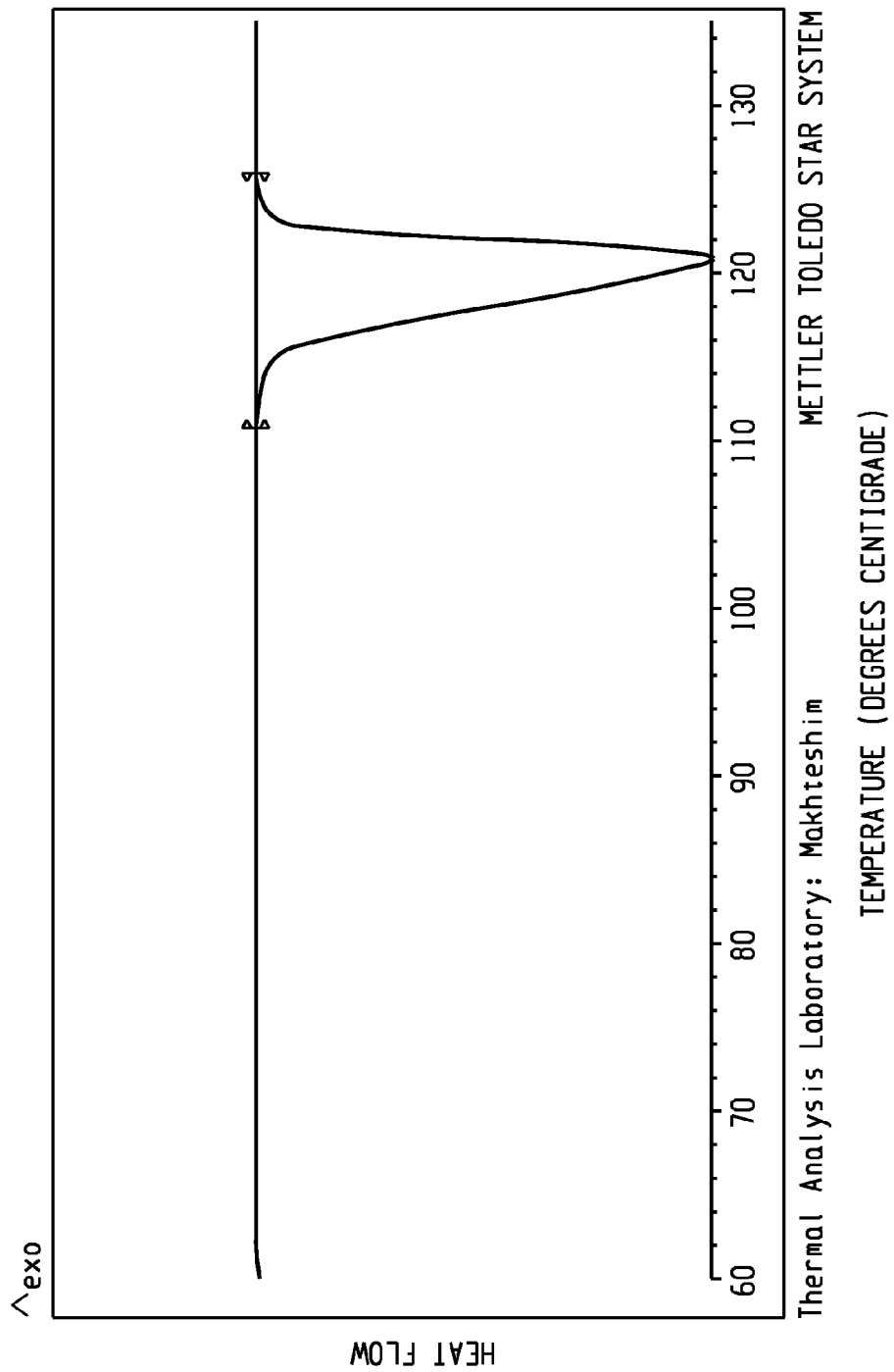
FIG. 3: is a Differential Scanning Calorimetry (DSC) thermogram of azoxystrobin A.

Furthermore, as shown in FIG. 3, Form A also exhibits a Differential Scanning Calorimetry (DSC) thermogram which is characterized by a predominant endotherm peak at a range of about 114-117° C. as measured by DSC of Mettler Toledo with 821$^e$ module. The weighted samples (2-4 mg) were purged with nitrogen flow during the measurements at a scan rate of 2 and/or 10° C. per minute. Aluminum standard pierced crucibles of 40 μL were used. The evaluation is performed using STAR$^e$ software. As used herein, the term "about 114-117° C." means a range of 110° C. to 120° C. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1.5° C.

Figure 4:
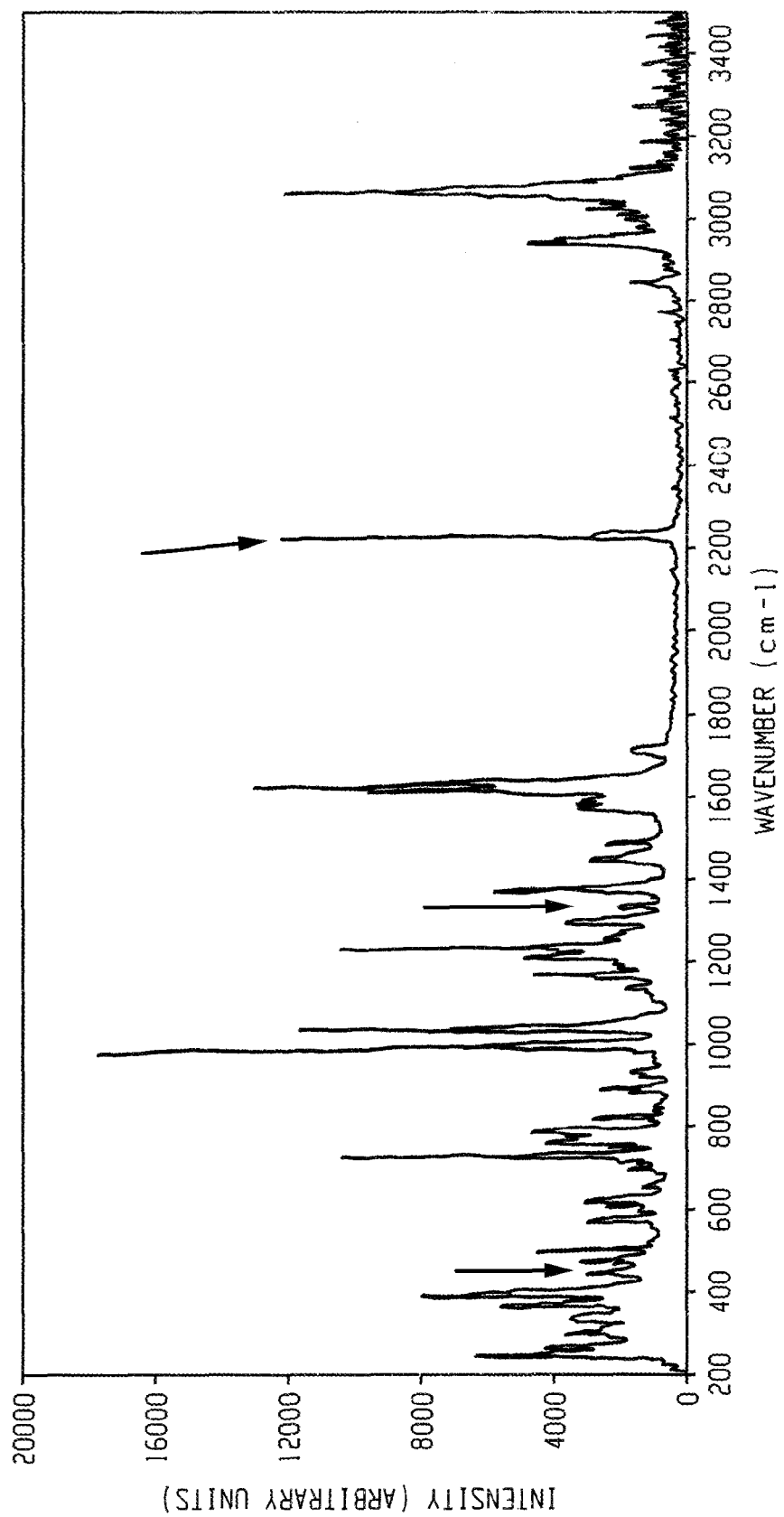
FIG. 4: is a Raman spectrum of azoxystrobin Form A.

Furthermore, as shown in FIG. 4, Form A also exhibits a Raman spectrum having characteristic peaks at about 4398, 133029 and 22332 cm$^{-1}$. Raman spectra were monitored using a confocal Raman microscope (Jobin Yvon Labram UV HR), driven by Labspec 4.04 software. In this system the Raman spectrometer is coupled to a microscope (Olympus BX 41). Raman scattering was excited by a diode laser at 784.79 nm with laser power of about 10 mW. The scattered light was then focused into a 0.8 m dispersive spectrometer, equipped with a 600 lines/mm grating and combined with an air cooled charged coupled device (CCD) for Raman signal detection. Spectra were monitored by focusing the laser beam manually on particular points in the crystals. The focusing was done by an ×50/0.75 microscope objective to spots of ~1.5 μm diameter. A confocal pinhole of 100 μm diameter, before the entrance slit to the spectrograph, rejected fluorescence and Raman signal from nut of focus planes. The spectra were collected in the 150-3500 cm$^{-1}$ range, while scanning the spectrum across the CCD by moving the grating seven times. The different spectral regions were accumulated over 180 s and each of them twice. The spectra were corrected for the contribution of the fluorescence background (not shown).

In another aspect, the present invention provides processes for preparing the novel azoxystrobin polymorph Form A. Form A azoxystrobin can be prepared by crystallizing azoxystrobin from a solvent selected from the group consisting an alcohol, an ether, a ketone, an ester, an amide, a nitrile, and an aliphatic or aromatic hydrocarbon; and isolating the resulting crystals. In a currently preferred embodiment, the solvent is selected from the group consisting of methanol, ethanol, tetrahydrofuran, acetone, ethylene glycol, acetonitrile, ethyl acetate, methyl isobutyl ketone, xylene and toluene. In another currently preferred embodiment, the process includes preparing a solution of the compound is one or more of the aforementioned solvents, preferably by applying heat until dissolution is complete, gradually cooling the solution until crystals appear, and isolating the crystals. Generally, cooling to room temperature is sufficient, however, the solution can be cooled to lower temperatures, for example 0° C., 5° C., 10° C., 15° C. and the like. Gradual cooling is typically achieved e.g., by removing the heat and allowing the solution to cool.

Also, the reaction can be seeded with Form A seeds in order to induce crystallization, as known in the art.

The azoxystrobin starting material used for preparing Form A can be any form of azoxystrobin, including azoxystrobin prepared in accordance with EP-A-0382375, EP-A-0242081 or U.S. Pat. No. 7,084,272, amorphous azoxystrobin, azoxystrobin Form B, a mixture of azoxystrobin Form A and Form B, or any other azoxystrobin known in the art.

Form B

In another embodiment, the present invention provides a novel crystalline polymorphic form of methyl (E)-2-{2-[6-(2-cyanophenoxy)pyrimidin-4-yloxy]phenyl}-3-methoxyacrylate(azoxystrobin), designated "Form B". This novel and surprising polymorph may be characterized by, for example, DSC, X Ray powder diffraction spectrometry, IR spectrometry and/or Raman spectrometry.

Figure 5:
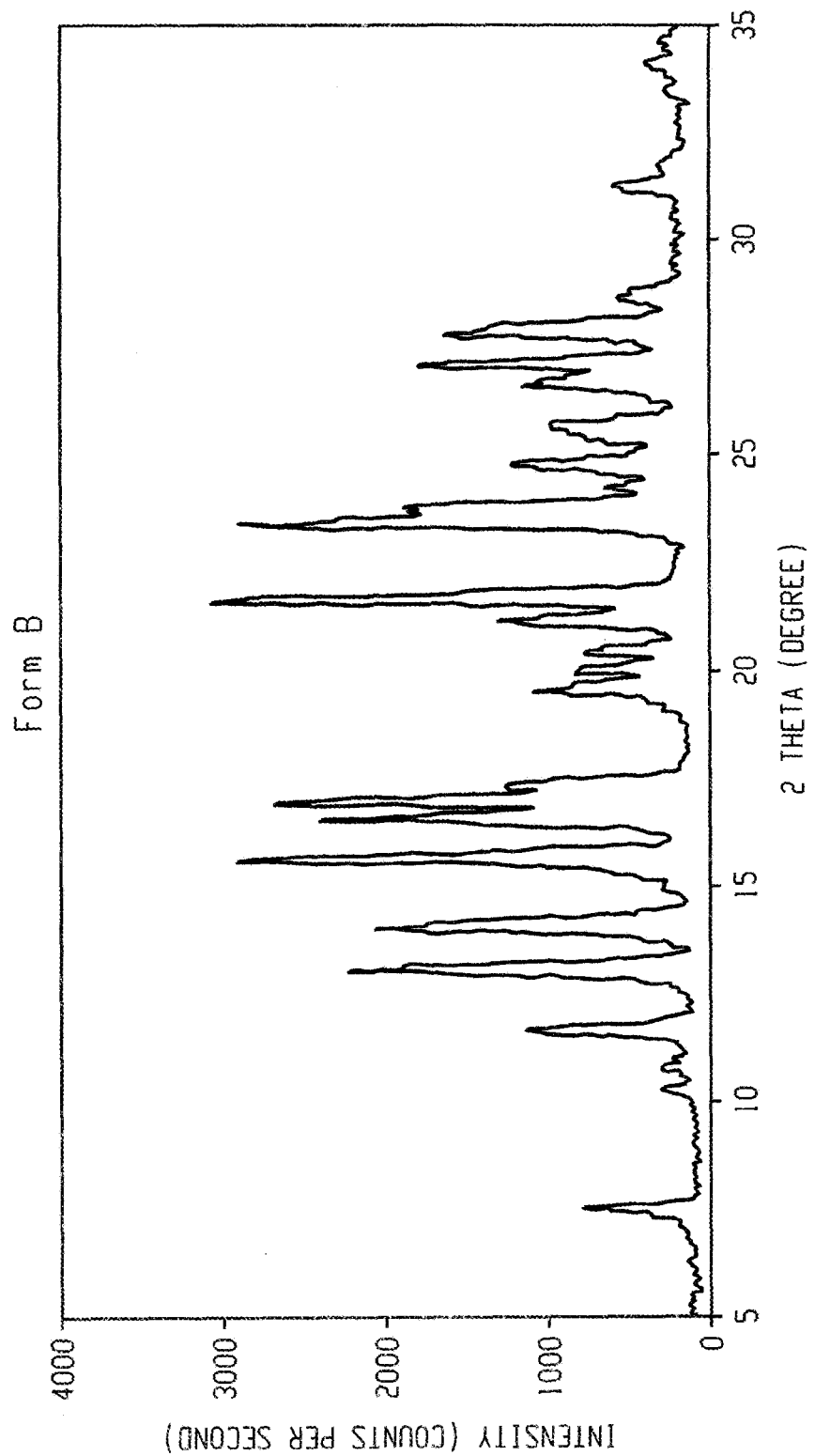
FIG. 5 is an X-ray powder diffraction spectrum of azoxystrobin Form B.

For example, as shown in FIG. 5, Form B exhibits an X-ray powder diffraction pattern having characteristic peaks (expressed in degrees 2θ (+/−0.2°θ) at one or more of the following positions: 7.5, 11.75, 13.20 and 19.65. Form B typically exhibits additional minor peaks at 14.15, 17.1 and 23.6 degrees 2θ (+/−0.2°θ). The X-Ray powder diffraction was measured as described above.

Figure 6:
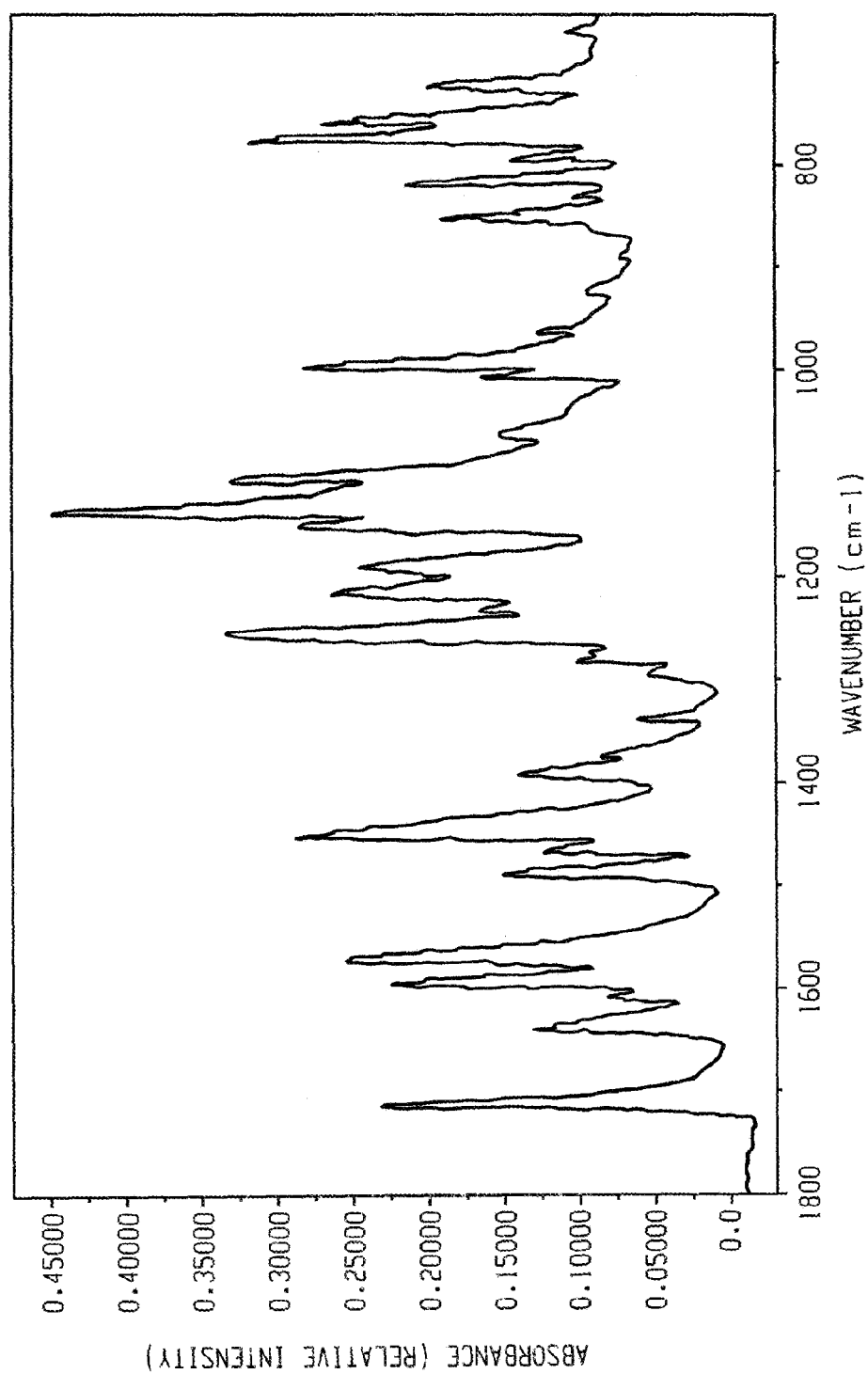
FIG. 6: is a FT Infrared spectrum of azoxystrobin Form B.
7: is a Differential Scanning Calorimetry (DSC) thermogram of azoxystrobin Form B.

Furthermore, as shown in FIG. 6, Form B also exhibits an Infrared (IR) spectrum having characteristic peaks at about 1389, 1335 and 1245 cm$^{-1}$, as measured by a Fourier transform infrared (FT-IR) spectrophotometer as described above.

Figure 7:
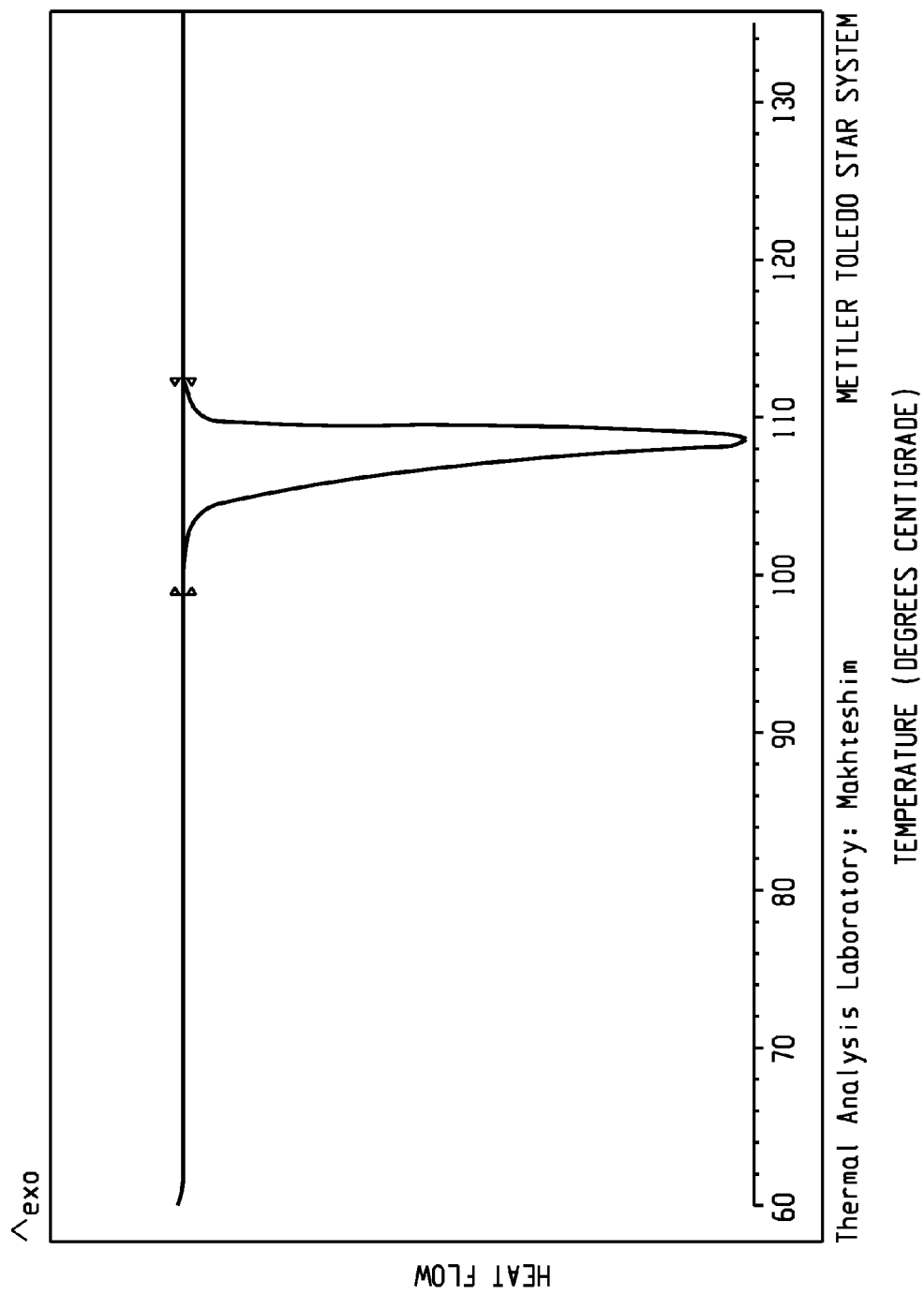

Furthermore, as shown in FIG. 7, Form B also exhibits a DSC thermogram which is characterized by monotropic system showing a predominant endotherm at a range of about 101-105° C. The thermogram was measured by a Differential Scanning Calorimeter as described above. As used herein, the term "about 101-105° C." means from 97° C. to about 108° C.

Figure 8:
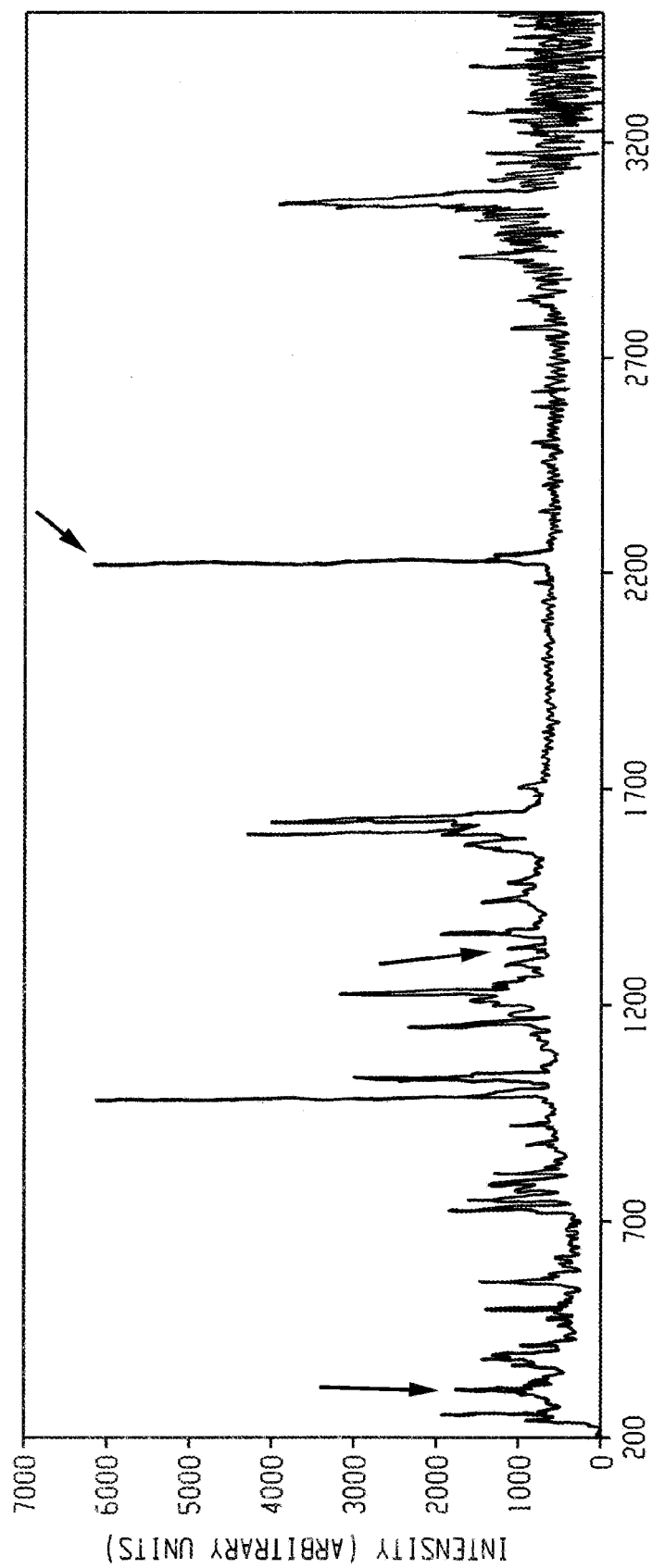
FIG. 8: is a Raman spectrum of azoxystrobin Form B.

Furthermore, as shown in FIG. 8, Form B also exhibits a Raman spectrum having characteristic peaks at about 3098, 1335 and 2237 cm$^{-1}$, measured by the method described above.

In another aspect, the present invention provides processes for preparing the novel polymorph Form B. Form B can be prepared by crystallizing azoxystrobin from a solvent mixture comprising water and an organic solvent selected from the group consisting of an alcohol and an amide; and isolating the resulting crystals. In a currently preferred embodiment, the organic solvent is selected from the group consisting of 1-propanol and N,N-dimethyl acetamide. In another currently preferred embodiment, the process includes preparing a solution of the compound is one or more of the aforementioned organic solvents, with or without applying heat until dissolution is complete, adding water, preferably pre-cooled so as to form crystals of the compound, and isolating the crystals. Generally, the water is pre-cooled for example to 0° C., 5° C., 10° C., 15° C. and the like.

The azoxystrobin starting material used for preparing Form B can be any form of azoxystrobin, including azoxystrobin prepared in accordance with EP-A-0382375, EP-A-0242081 or U.S. Pat. No. 7,084,272, amorphous azoxystrobin, azoxystrobin Form A, a mixture of azoxystrobin Form A and Form B, or any other azoxystrobin known in the art.

Form A and Form B Mixtures

In yet another embodiment, the present invention provides a mixture of polymorphic Form A and Form B of methyl (E)-2-{2-[6-(2-cyanophenoxy)pyrimidin-4-yloxy]phenyl}-3-methoxyacrylate(azoxystrobin).

Figure 9:
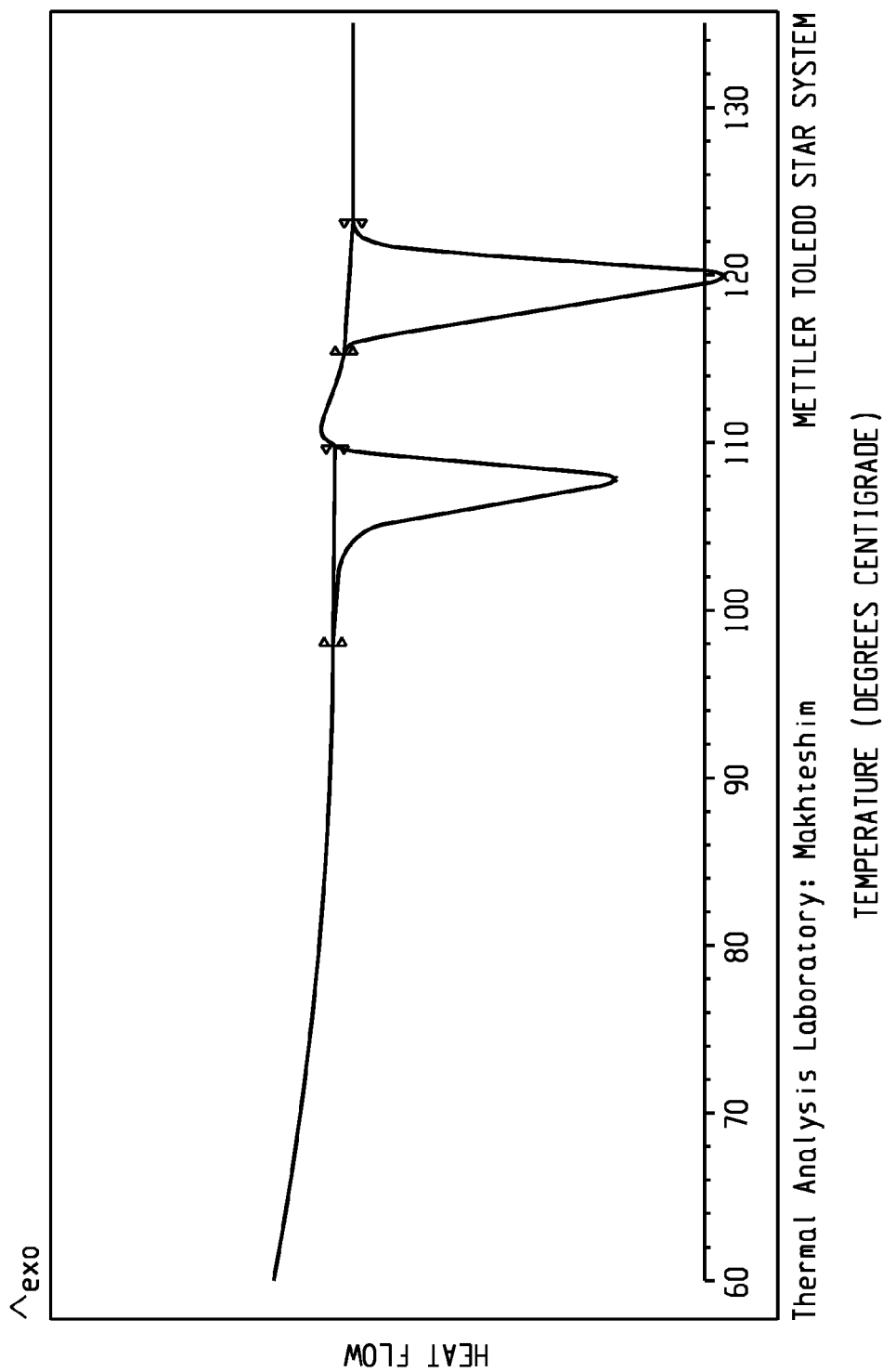
FIG. 9: is a Differential Scanning Calorimetry (DSC) thermogram of an azoxystrobin Form A and B mixture.

The mixture exhibits a Differential DSC thermogram substantially as shown in FIG. 9, as measured by Differential Scanning Calorimeter as described above.

In another aspect, the present invention provides processes for preparing a mixture of azoxystrobin Form A and Form B. A mixture of Form A and Form B azoxystrobin can be prepared by crystallizing azoxystrobin from a solvent mixture comprising an alcohol (e.g., isopropyl alcohol, 1-propanol and butanol) and an anti-solvent selected from an aliphatic and aromatic hydrocarbon (e.g., heptane); and isolating the resulting crystals. In a currently preferred embodiment, the process includes preparing a solution of azoxystrobin is an alcohol, preferably by applying heat until dissolution is complete, adding the anti-solvent so as to form crystals of the compound, and isolating the crystals. The reaction can also be cooled to induce precipitation. Generally, cooling to room temperature is sufficient, however, the solution can be cooled to lower temperatures, for example 0° C., 5° C., 10° C., 15° C. and the like.

In another embodiment, a mixture of Form A and Form B azoxystrobin can be prepared by a) preparing a solution of methyl (E)-2-{2-[6-(2-cyanophenoxy)pyrimidin-4-yloxy] phenyl}-3-methoxyacrylate in an alcohol (e.g., isopropyl alcohol); b) rapidly cooling the solution so as to form crystals of said compound; and isolating the crystals. By "rapid cooling" it is meant that the solution is contacted with a cold medium (e.g., a chilled water bath or an ice bath) so as to achieve a rapid decrease in temperature which induced formation of crystals comprising a mixture of Form A and Form B azoxystrobin.

The azoxystrobin starting material used for preparing the Form A and Form B mixture can be any form of azoxystrobin, including azoxystrobin prepared in accordance with EP-A-0382375, EP-A-0242081 or U.S. Pat. No. 7,084,272, amorphous azoxystrobin, azoxystrobin Form A, azoxystrobin Form B, or any other azoxystrobin known in the art.

Amorphous Azoxystrobin

In another embodiment, the present invention provides a novel amorphous azoxystrobin. This novel and surprising amorphous form may be characterized by, for example, X-Ray powder diffraction spectrometry.

Figure 10:
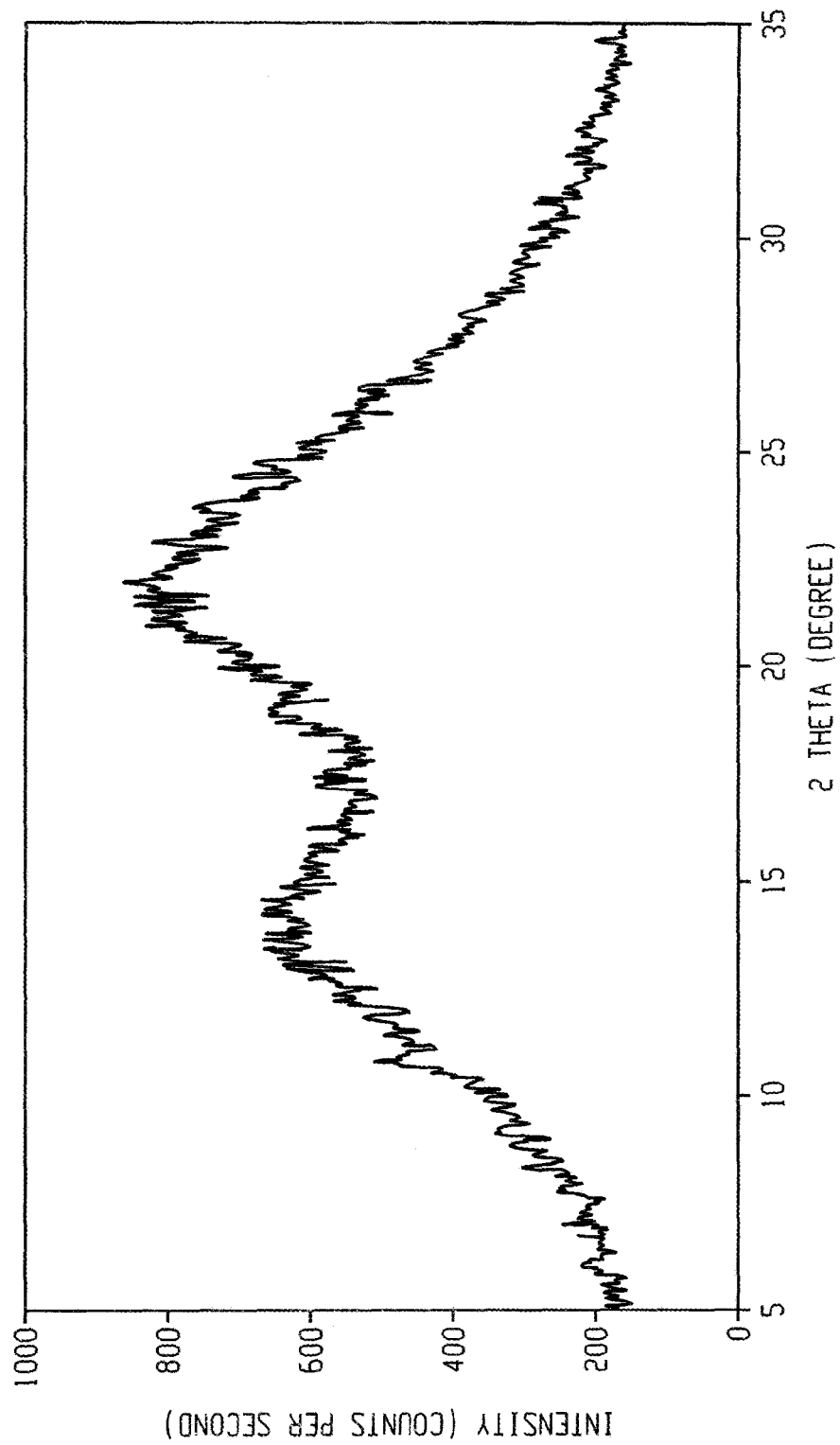
FIG. 10: is an X-ray powder diffraction spectrum of amorphous azoxystrobin.

For example, as shown in FIG. 10, the amorphous form has an X-ray powder diffraction pattern showing no significant signals, indicating an amorphous azoxystrobin solid.

In another aspect, the present invention provides processes for preparing the novel amorphous azoxystrobin. In one embodiment, amorphous azoxystrobin is prepared by heating azoxystrobin to a temperature greater than its melting point (preferably to a temperature greater than about 100° C., more preferably to a temperature of about 120° C.), and very fast cooling (e.g. quench cooling).

The azoxystrobin starting material used for preparing the amorphous azoxystrobin can be any form of azoxystrobin, including azoxystrobin prepared in accordance with EP-A-0382375, EP-A-0242081 or U.S. Pat. No. 7,084,272, azoxystrobin Form A, azoxystrobin Form B, mixtures of Form A and Form B, or any other azoxystrobin known in the art.

Compositions and Uses

Azoxystrobin is known impart excellent effect for combating noxious pests including, but not limited to: Anthracnose (*Colletotrichum graminicola*), Brown Patch (*Rhizoctonia solani*), Cool Weather Brown Patch (*Rhizoctonia cerealis*), Fusarium Patch (*Microdochium nivale*), Gray Snow Mold (*Typhula* spp.), Leafspot (*Drechslera* spp. and/or *Bipolaris* spp.), Melting Out (*Drechslera* spp. and/or *Bipolaris* spp.), Necrotic Ring Spot (*Leptosphaeria korrae*), Pink Snow Mold (*Microdochium nivale*), Pythium Blight (*Pythium* spp.), Pythium Root Rot (*Pythium* spp.), Red Thread (*Laetisaria fuciformis*), Rhizoctonia Large Patch (*Rhizoctonia solani*), Spring Dead Spot (*Leptosphaeria korrae* or *Gaeumannomyces graminis*), Summer Patch (*Magnaporthe poae*), Take-all Patch (*Gaeumannomyces graminis*), Yellow Patch (*Rhizoctonia cerealis*), and Zoysia Patch (*Rhizoctonia solani* and/or *Gaeumannomyces incrustana*), Ascomcetes (e.g., powdery mildews), diomycetes (eg rusts), Deutoromycetes (e.g., rice blast) and Oomycetes (e.g., downy mildew)( Thus, in one embodiment, the present invention also provides compositions comprising the novel crystalline polymorphs or amorphous forms, which are useful for controlling and combating noxious living grown on agricultural and horticultural crops and up-land, especially fungus. In one embodiment, the composition comprises a crystalline polymorph Form A of azoxystrobin; and an acceptable adjuvant. In another embodiment, the composition comprises a crystalline polymorph Form B of azoxystrobin and an acceptable adjuvant. In yet another embodiment, the composition comprises a mixture of a crystalline polymorph Form A and Form B of azoxystrobin; and an acceptable adjuvant. In one embodiment, the composition comprises amorphous azoxystrobin; and an acceptable adjuvant.

The present invention also relates to methods for combating fungus, comprising applying to a plant, to the seed of the plant or to the locus of a seed or plant a fungicidally effective amount of the compositions of the invention.

The present invention also relates to methods for protecting crops and upland, including industrial products thereof, such as seeds and fruits, by applying to the crops or products thereof an effective amount of the compositions of the invention.

The concentration of the azoxystrobin for use in the compositions of the present invention will depend upon object noxious livings, the method of application, and the form of the composition and the dose of the active ingredient. The concentration is not critical and it is usually in a range of about 1 to 10,000 ppm, preferably about 20 to 2,000 ppm.

The composition can be prepared in a variety of forms such as dust, wettable powder, emulsifiable concentrate, inert emulsion, oil solution, aerosol preparation, etc. with adjuvants as the cases of agricultural compositions. The composition can be applied with or without diluting them in suitable concentrations.

Suitable adjuvants include powdery carries such as talc, kaolin, bentonite, diatomaceous earth, silicon dioxide, clay and starch; liquid diluents such as water, xylene, toluene, dimethylsulfoxide, dimethylformamide, acetonitrile, and alcohol; emulsifiers dispersing agents, surfactants such as sodium alkyl benzene sulfonate, polyoxyethylene alkylaryl ether, sodium naphthalene sulfonate formaldehyde condensate, calcium ether sulfate, polyoxyethyleneglycol dodecylphenyl ether, polyoxyethylene lauryl ether, polyoxyethylene fatty acid ester, sodium alkylsulfate, sulfate of polyoxyethylene alkylaryl ether and di-alkylsulfosuccinate etc.

The concentration of the active ingredient in the composition is usually 5 to 80 wt. % in the case of the oily concentrate; and 0.5 to 30 wt. % in the case of dust; 5 to 60 wt. % in the case of wettable powder. It is also possible to combine with the other agricultural ingredients such as the other insecticides, acaricides, and/or plant growth regulators. Sometimes synergistic effects are found. The other agricultural ingredients include organic phosphoric acid ester type compounds, carbamate type compounds, dithio (or thiol) carbamate type compounds, organic chlorine type compounds, dinitro type compounds, organic sulfur or organometallic type compounds, antibiotics, substituted diphenyl ether type compounds, urea type compounds, triazine type compounds, benzoylurea type compounds, pyrethroid type compounds, imide type compounds and benzimidazole type compounds and more particularly, benzoylurea type insecticides such as N-(2, 6-difluorobenzoyl)-N'-(p-chlorophenyl)urea; pyrethroid type insecticides such as .alpha.-cyano-3-phenoxybenzyl-2-(4-chlorophenyl)isovalerate; imide type germicides such as N-(3,5-dichlorophenyl)-1,2-dimethylcyclopropane-1,2-dicarboximide; benzimidazole type germicides such as methyl-1-(butylcarbamoyl)-2-benzimidazolecarbamate; thiocarbamate type geiiuicides such as S-ethyl N-(3-dimethylaminopropyl)thiocarbamate hydrochloride; dithiocarbamate type germicides such as manganese ethylenebisdithiocarbamate; and urea type germicides such as 2-cyano-N-(ethylaminocarbonyl)-2-(methoxyimino)acetamide.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

Experimental Details Section

EXAMPLE 1

Preparation of Azoxystrobin Form A

Azoxystrobin (10 g.) was dissolved in 50 ml. of isopropyl alcohol in Erlenmeyer with magnetic stirring at reflux for 10 minutes. The resulting clear solution was slowly cooled to 54° C. and left at that temperature for 10 minutes. The resulting crystalline solid was filtered and dried at 40° C. in the oven.

EXAMPLE 2

Preparation of Azoxystrobin Form A

Azoxystrobin was crystallized from the solvents listed in Table 1. Azoxystrobin is crystallized by forming a clear solution of Azoxystrobin by heating to reflux for 1-2 hrs. The solution was then cooled to room temperature and the forming crystals were filtered out and dried in the oven at 40-50° C. for 24 hrs.

TABLE 1

| Solvent | Ratio of solvent (ml):Azoxystrobin (g) | Precipitation time |
| --- | --- | --- |
| Ethanol | 9 | Rapid |
| Methanol | 7.5 | 1 day |
| Tetrahydrofuran | 5 | Rapid |
| Acetone | 2.5 | Rapid |
| Ethylene glycol | 5 | Rapid |
| Acetonitrile | 5 | Rapid |
| Ethyl acetate | 5 | Rapid |
| Methyl Isobutyl Ketone | 5 | 3 days |
| Xylene | 5 | Rapid |
| Toluene | 2.8 | Rapid |

EXAMPLE 3

Preparation of Azoxystrobin Form B

Azoxystrobin (2 g.) was dissolved in 10 ml of isopropyl alcohol in Erlenmeyer at reflux for 1 hour with vigorous magnetic stirring. The solution was then removed from the heating plate and cold water were dosed until cloud point (7.3 g.). The resulting light slurry was cooled to RT and the white crystalline matter was filtered out and dried at 40° C. in the oven.

EXAMPLE 4

Preparation of Azoxystrobin Form B

Azoxystrobin (2 g.) was dissolved in 10 ml of 1-Propanol in Erlenmeyer at reflux for 1 hour with vigorous magnetic stirring. The solution was then removed from the heating plate and cold water were added until cloud point and beyond it (15.6 g.). The resulting light slurry was cooled to RT and the white crystalline matter was filtered out and dried at 40° C. in the oven.

EXAMPLE 5

Preparation of Azoxystrobin Form B

Azoxystrobin (162 g.) was added to 300 g. of N,N-Dimethyl acetamide in a reactor of 1 liter at 500-850 rpm and 25° C. After the completion of the dissolution, 200 g. of water were dosed during 20-120 minutes. The slurry was stirred for 15 minutes and filtered out. The filtered solid was dried at 40° C. in the oven.

EXAMPLE 6

Preparation of a Mixture of Azoxystrobin Form A and Form B

Azoxystrobin (2.1 g.) were dissolved in 12 ml of isopropyl alcohol in Erlenmeyer at reflux for 1 hour, with magnetic stirring. At these conditions, 7 ml of n-Heptane were added dropwise and the Erlenmeyer was removed from the heating plate. After 3 minutes the solution becomes cloudy. After cooling to RT the resulted slurry was filtered out and dried at 40° C. in the oven.

EXAMPLE 7

Preparation of a Mixture of Azoxystrobin Form A and Form B

Azoxystrobin (2.1 g.) were dissolved in 12 ml of Butanol in Erlenmeyer at reflux for 1 hour, with magnetic stirring. At these conditions, 7 ml of n-Heptane were added dropwise and the Erlenmeyer was removed from the heating plate. After 2 minutes the solution becomes cloudy. After cooling to RT the resulted slurry was filtered out and dried at 40° C. in the oven.

EXAMPLE 8

Preparation of a Mixture of Azoxystrobin Form A and Form B

Azoxystrobin (2 g.) were dissolved in 10 ml Isopropyl alcohol at reflux in Erlenmeyer with magnetic stirring for 10 minutes. The solution was removed from the heating plate and at a temperature of 67° C. the cloudy solution was transferred to ice-water medium bath for rapid cooling. The resulting slurry was then filtered out and the crystalline matter was dried at 40° C. in the oven.

EXAMPLE 9

Preparation of Amorphous Azoxystrobin

Azoxystrobin (1 g.) was heated in a 250 ml beaker over heating plate until melt. The hot magma (at ~120° C.) was kept heated for further 10 minutes and then immediately placed in an ice-acetone bath (−15° C.) for rapid cooling. The amorphous glass-like solid was analyzed in X-ray powder diffraction. the obtained difractogram exhibit no distinct peaks.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. Crystalline polymorph Form B of (E)-2-{2-[6-(2-cyanophenoxy)pyrimidin-4-yloxy]phenyl}-3-methoxyacrylate exhibiting an X-ray powder diffraction pattern having characteristic peaks expressed in degrees 2θ (+/−0.20° θ) at about 7.5, 11.75, 13.20 and 19.65.

2. The crystalline polymorph according to claim 1, wherein the polymorph further exhibits characteristic peaks expressed in degrees 2θ (+/−0.20° θ) at about 14.15, 17.1 and 23.6.

3. The crystalline polymorph according to claim 1, wherein the polymorph exhibits an X-ray powder diffraction pattern substantially as shown in FIG. 5.

4. The crystalline polymorph according to claim 1, wherein the polymorph exhibits an infrared (IR) spectrum substantially as shown in FIG. 6.

5. The crystalline polymorph according to claim 1, wherein the polymorph exhibits a Differential Scanning Calorimeter (DSC) thermogram substantially as shown in FIG. 7.

6. The crystalline polymorph according to claim 1, wherein the polymorph exhibits a Raman spectrum having characteristic peaks at about 3098, 1335 and 2237 $cm^{-1}$.

7. The crystalline polymorph according to claim 1, wherein the polymorph exhibits a Raman spectrum substantially as shown in FIG. 8.

8. A process for the preparation of a crystalline polymorph Form B of 3(E)-2-{2-[6-(2-cyanophenoxy)pyrimidin-4-yloxy]phenyl}-3-methoxyacrylate, the process comprising the steps of crystallizing said compound from a solvent mixture comprising water and an organic solvent selected from the group consisting of an alcohol, and an amide.

9. The process according to claim 8, wherein the organic solvent is selected from the group consisting of 1-propanol and N,N-dimethyl acetamide.

10. The process according to claim 8, comprising the steps of:
   a) preparing a solution of (E)-2-{2-[6-(2-cyanophenoxy)pyrimidin-4-yloxy]phenyl}-3-methoxyacrylate in a solvent selected from the group consisting of an alcohol and an amide;
   b) adding water to said solution so as to form crystals of said compound; and
   c) isolating the crystals.

11. A composition for combating fungus which comprises a crystalline polymorph Form B of (E)-2-{2-[6-(2-cyanophenyoxy)pyrimidin-4-yloxy]phenyl}-3-methoxyacrylate according to claim 1; and an acceptable adjuvant.

12. A method for combating fungus in a plant, comprising applying to the plant, to a seed of the plant or to the locus of the seed or the plant a fungicidally effective amount of the composition of claim 11.

13. A method for protecting crops from fungus, comprising applying to the crops an effective amount of the composition of claim 11.

14. The crystalline polymorph Form B of (E)-2-{2-[6-(2-cyanophenyoxy)pyrimidin-4-yloxy]phenyl}-3-methoxyacrylate of claim 1 further exhibiting an infrared (IR) spectrum characteristic peaks at about 1389, 1335 and 1245 $cm^{-1}$.

15. The crystalline polymorph Form B of (E)-2-{2-[6-(2-cyanophenyoxy)pyrimidin-4-yloxy]phenyl}-3-methoxyacrylate of claim 1 further exhibiting a predominant endotherm at a range of about 101-105° C. as measured by a Differential Scanning Calorimeter (DSC) at a scan rate of 10° C. per minute.

16. The crystalline polymorph Form B of (E)-2-{2-[6-(2-cyanophenyoxy)pyrimidin-4-yloxy]phenyl}-3-methoxyacrylate of claim 1 further exhibiting both of the following characteristics:
   (a) an infrared (IR) spectrum having characteristic peaks at about 1389, 1335 and 1245 $cm^{-1}$; and
   (b) a predominant endotherm at a range of about 101-105° C. as measured by a Differential Scanning Calorimeter (DSC) at a scan rate of 10° C. per minute.

17. A composition for combating fungus which comprises a crystalline polymorph Form B of methyl(E)-2-{2-[6-(2- cyanophenyoxy)pyrimidin-4-yloxy]phenyl}-3-methoxy-acrylate according to any one of claims 14-16; and an acceptable adjuvant.

\* \* \* \* \*

UNITED STATES PATENT AND TRADEMARK OFFICE
CERTIFICATE OF CORRECTION

PATENT NO.      : 8,546,411 B2                                    Page 1 of 1
APPLICATION NO. : 12/525362
DATED           : October 1, 2013
INVENTOR(S)     : Zamir et al.

It is certified that error appears in the above-identified patent and that said Letters Patent is hereby corrected as shown below:

In the claims:

Claim 1, Col. 11, Lines 59-61, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Claim 8, Col. 12, Lines 14-19, please delete the first number "3" from "3(E)-2-{2-[6-(2-cyanophenoxy)pyrimidin-4-yloxy] phenyl}-3-methoxyacrylate" to read "(E)-2-{2-[6-(2-cyanophenoxy)pyrimidin-4-yloxy]phenyl}-3-methoxyacrylate".

Claim 17, Col. 12, Line 67 and Col. 13, Line 1-2, please insert a space between "methyl" and "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,546,411 B2
APPLICATION NO. : 12/525362
DATED : October 1, 2013
INVENTOR(S) : Zamir et al.

It is certified that error appears in the above-identified patent and that said Letters Patent is hereby corrected as shown below:

In the claims:

Claim 1, Col. 11, Lines 59-61, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Claim 8, Col. 12, Lines 18-19, please delete the first number "3" from "3(E)-2-{2-[6-(2-cyanophenoxy)pyrimidin-4-yloxy] phenyl}-3-methoxyacrylate" to read "(E)-2-{2-[6-(2-cyanophenoxy)pyrimidin-4-yloxy]phenyl}-3-methoxyacrylate".

Claim 8, Col. 12, Lines 18-19, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Claim 14, Col. 12, Lines 47-49, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Claim 15, Col. 12, Lines 51-53, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

Claim 16, Col. 12, Lines 57-59, please insert --methyl-- before "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".

This certificate supersedes the Certificate of Correction issued February 18, 2014.

Signed and Sealed this
Twenty-second Day of April, 2014

Michelle K. Lee
*Deputy Director of the United States Patent and Trademark Office*

Claim 17, Col. 12, Line 67 and Col. 13, Line 1-2, please insert a space between "methyl" and "(E)-2-{2-[6-(2-cyanophenoxy)pyrimidin-4-yloxy] phenyl}-3-methoxyacrylate" to read "methyl (E)-2-{2-[6-(2-cyanophenoxy)pyrimidin-4-yloxy] phenyl}-3-methoxyacrylate".